United States Patent [19]

Kingdon et al.

[11] Patent Number: 5,354,682
[45] Date of Patent: Oct. 11, 1994

[54] VIRAL-SAFE PURIFIED HUMAN THROMBIN

[75] Inventors: Henry S. Kingdon, Pasadena; Michael J. Griffith, Walnut; Joyce Lawrence, Claremont, all of Calif.; Roger L. Lundblad, Chapel Hill, N.C.

[73] Assignee: Baxter International Inc., Deerfield, Ill.

[21] Appl. No.: 23,143

[22] Filed: Feb. 24, 1993

Related U.S. Application Data

[63] Continuation of Ser. No. 481,528, Feb. 20, 1990, abandoned.

[51] Int. Cl.$^5$ .................. C12N 9/74; A61K 35/14; A61K 37/475
[52] U.S. Cl. .................................... 435/214; 530/381; 530/384
[58] Field of Search ................. 435/214; 530/381, 384

[56] References Cited

U.S. PATENT DOCUMENTS

| | | | |
|---|---|---|---|
| 2,495,298 | 1/1950 | Szent-Gyongyi | 530/384 |
| 4,137,127 | 1/1979 | Stocker | 435/219 |
| 4,170,590 | 10/1979 | Stephan et al. | 530/384 |
| 4,315,919 | 2/1982 | Shanbrom | 530/384 |
| 4,380,511 | 4/1983 | Manuzza et al. | 435/214 |
| 4,774,076 | 9/1988 | Gomi et al. | 424/49 |
| 4,960,702 | 10/1990 | Rice et al. | 435/212 |

FOREIGN PATENT DOCUMENTS 1527261 12/1989 U.S.S.R. ................. 435/214

OTHER PUBLICATIONS

Fenton et al., *Human Thromburn* J. of Biol. Chem., vol. 252, No. 11, pp. 3587–3598, 1977.
Boissel et al., *Covalent Structures . . .*, J. of Biol. Chem., vol. 259, No. 9, pp. 5691–5697, 1984.
Sigma Catalog, Thrombin, p. 245, 1985.
Sigma Catalog, pp. 172 and 173.
Lundblad, A Rapid Method for the Purification of Bovine Thrombin and the Inhibition of the Purified Enzyme with Phenylmethyl–sulfonyl Flouride, Studies on Bovine Thrombin, Biochemistry, vol. 10, No. 13, 1971, pp. 2501–2506.
Nordenman, et al., Thrombosis Research, vol. 11, Purification of Thrombin of Affinity Chromatography on Immobilized Heparin, 1977, pp. 799–808, 1977.
Thompson, et al., Biochimica et Biophysica Acta, Affinity Chromatography of Thrombin, 1971, pp. 210–215.
Muller et al., High–Performance Affinity Chromatography of Human Thrombin on Modified Polystyrene Resins, Journal of Chromatography, 359, 1986, pp. 351–357.
Fenton, II, et al., Human Thrombin: Preparative Evaluation, Structural Propereites, and Enzymic Specificity, Chemiotry & Physiology of Human Plasma Proteins, 1979, pp. 151–183.
F. Brosstad, Purification, Characterization and Insolubilization of Bovine Thrombin, Thrombosis Research, vol. 11, 1977, pp. 119–130.
Fischer, et al., Thrombin Purification by One–Step Preparative Affinity Chromatography on Modified Polystyrenes, Journal of Chromatography, 1986, pp. 95–100.

(List continued on next page.)

*Primary Examiner*—David M. Naff
*Assistant Examiner*—Michael V. Meller
*Attorney, Agent, or Firm*—Spensley Horn Jubas & Lubitz

[57] ABSTRACT

A purified therapeutic grade thrombin is described which is essentially free of lipid envelope viruses, has a specific activity of about 2200 NIH units per milligram of protein to about 3200 NIH units per milligram of protein, is essentially homogeneous and may be produced on a commercial-scale. The thrombin is acceptable from human administration.

1 Claim, 1 Drawing Sheet

OTHER PUBLICATIONS

Gaida, et al., Affinity Chromatography of Human Thrombin on Modified Silica, Journal of Chromatography, 1988, pp. 385–391.

Hatton, et al., The Affinity of Human, Rabbit and Bovine Thrombins for Sepharose-lysine and Other Conjugates, Biochimica et Biophysica Acta, 1976, pp. 575–585.

Hixson, et al., Affinity Chromatography: Purification of Bovine Trypsin and Thrombin, Archives of Biochemistry and Biophysics, 1973, pp. 501–509.

Miller-Andersson, et al., Preparation and Stability of a Highly Purified Human Thrombin Standard, Thrombosis Research, 20, 1980, pp. 109–122.

Pepper, et al., Chromatography of Human prothrombin Complex on Dextran Sulphate Agarose, thrombosis Research, vol. II, 1977, pp. 687–692.

Thompson, High Affinity Binding of Human and Bovine Thrombins to p-chlorobenzylamide-$\epsilon$-Aminocaproyl Agarose, Biochmica et Biophysics Acta, 1976, pp. 200–209.

Workman, Jr., et al., On the Preparation of Bovine $\alpha$-Thrombin, Thrombos, Haemostas., 1978, pp. 193–199.

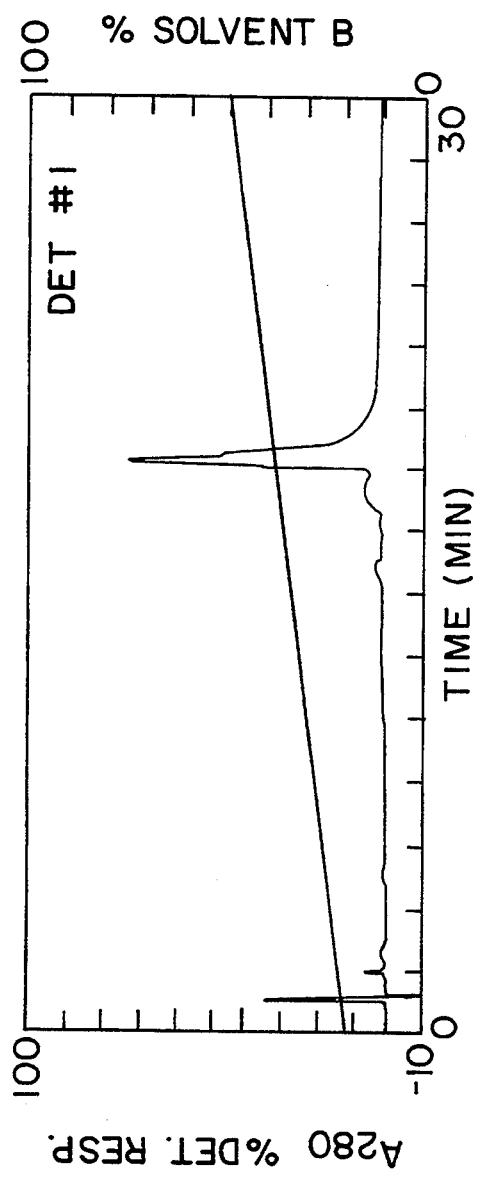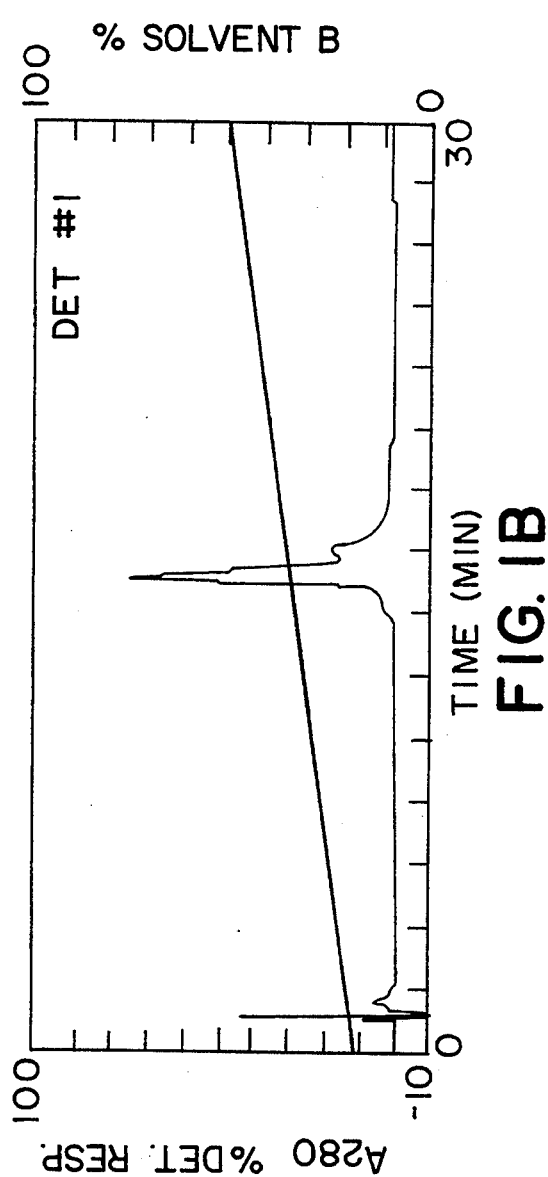

VIRAL-SAFE PURIFIED HUMAN THROMBIN

This is a continuation of application Ser. No. 481,528 filed on Feb. 20, 1990, now abandoned.

FIELD OF THE INVENTION

The present invention relates to the purification of human thrombin. More specifically it relates to the purification and recovery of human thrombin produced in commercial-scale quantities for use as a therapeutic agent in several human applications.

BACKGROUND OF THE INVENTION

Thrombin is a highly specific enzyme catalyzing the proteolytic cleavage of fibrinogen to fibrin in blood congulation. Thrombin is also involved in cleavage of a 37 residue amino acid peptide from Factor XIII which, upon activation, catalyzes formation of the intramolecular gamma-glutamyl-lysine bridges cross-linking fibrin molecules. Thrombin is generated from its precursor prothombin, and several molecular forms (depending on the extent of cleavage) have been identified. If available, therapeutically purified human thrombin would have many beneficial applications. For example, human thrombin can be effectively used as a topical agent to promote coagulation. It can be incorporated into a polymer structure for use as a wound dressing. A still further application is in compositions known as fibrin glue in which thrombin and fibrin contained in separate capsules are combined for immediate application to fresh wounds, particularly surgical incisions.

Bovine thrombin was first purified in analytical quantities by Rasmussen utilizing an ion exchange resin IRC-50 (P. S. Rasmussen, *Biochem. Biophys. Acta*, 16, 157 (1955). Strassle, et al., *Biochem. Biophys. Acta*, 73, 462 (1983) purified thrombin on DEAE-cellulose to obtain a preparation of high specific activity (2100 NIH units/mg), and also discovered that such high specific activity could be attained if the thrombin was first produced from its zymogen.

Conversion of prothrombin to thrombin by proteolysis is dramatically increased in the presence of a phospholipid bilayer, calcium ions, and Factor V. For a general review of the biochemistry of thrombin formation, see Bloom & Thomas, *Hemostasis and Thrombosis*, 2 ed., (Churchill Livingstone, 1987). Accordingly, purification schemes in which the thrombin is derived from proteolytic conversion of prothrombin must include factors promoting such conversion. Alternatively, the lipoprotein thromboplastin may be utilized to activate Factor VII which in turn catalyzes formation of the Factor Xa mediating conversion of prothrombin to thrombin.

Other purification techniques are known in the art. Thompson & Davie, *Biochem, Biophys. Acta*, 250, 210 (1971) purified thrombin by affinity chromotography on p-chlorobenzyl amino-e-aminocaproyl agarose. Schmer, Hoppe-Sejler's, *Z. Physiol. Chem.*, 353, 810 (1972) utilized a combination of ion exchange and affinity chromatography. All of these methods involve purification of thrombin from bovine plasma, which is a readily available and inexpensive source for analytical study.

There are, of course, serious limitations to the use of bovine thrombin in human therapeutic applications. First, the impurities present in bovine preparations include bovine proteins which are antigenic. Secondly, bovine thrombin itself, like other proteins of animal origin for which a homologous human species exists, may cause anaphylactic reactions, even when applied topically (see *Thrombosis Research*. 53, 277 (1989). The lack of a high purity preparation of human thrombin has frustrated attempts to use thrombin as a local hemostat in eye surgery (see Aaberg, *Am. J. Opthomology*, 106, 485 (1988), because of adverse reactions.

In the field of the purification of human thrombin, which differs molecularly from the bovine equivalent, less research has been done. At present there are two basic approaches to purification. One approach was developed by Fenton, et al., *Chemistry and Physiology of Human Plasma*, ed. D. H. Bing, Pergammon Press: NY (1979), utilizing polymethyl acrylic acid which reportedly has a quantitative adsorption affinity for thrombins and can be used to selectively separate the beta and gamma species of thrombin from the alpha species. As noted by this investigator, human thrombin obtained in this procedure tends to be unstable and very prone to autolytic degradation.

The second basic approach utilizes a sulfated polysaccaride matrix to selectively sorb thrombin, Lundblad, *Biochemistry*, 10, 2501 (1971). While this matrix yields a thrombin product of high specific activity, the use of the sulfated Sephadex® matrix is unsuitable for production of therapeutic-grade thrombin. The Sephadex® derivative is a fine powder with the adverse characteristic of wide fluctuations in swelling and shrinking under various solvent conditions. It is also very difficult to prevent contaminating powder fines from being introduced into the final product.

Other purification methods have been reported more recently. Mullen and Yu, *J. Chromatography*, 359, 351 (1986) describe a method of purifying thrombin on cross-linked polystyrenes modified with L-arginyl methylester which mimics the emzymatic binding of thrombin substrates. The method is particularly advantageous for analysis of very small amounts of thrombin prone to degradation. An improved purification technique was reported by Nordenman et al., *Thrombosis Research*, 11, 799 (1979) involving affinity chromatography on heparin immobilized onto agarose. The thrombin product appeared to be of greater purity upon electrophoresis than that obtained by some previous methods, but there was no indication that this technique or that described by Muller and Yu can be adapted to large-scale production.

SUMMARY OF THE INVENTION

The present invention relates to a viral-safe therapeutic thrombin for use in treating humans, and a process for isolating same. The therapeutic thrombin is characterized in being substantially homogeneous, having less than 10 pg total nucleic acids per dose, having low levels of other blood coagulation factors, inactivated thrombin, and prothrombin fragments, having an acceptably low level of viricidal agents, having a high specific activity, and being substantially nonpyrogenic. It is contemplated that the process be readily adaptable to large-scale production. Accordingly, it is an object of the present invention to utilize only those process steps which are capable of being scaled up to commercial levels. It is a further object to produce a therapeutic-grade thrombin product suitable for a wide range of medical applications. A still further object is to produce a purified thrombin product which is stable and will not lose specific activity through autolytic or other enzyme degradation.

The process of isolating the therapeutic-grade thrombin comprises:

a) sorbing the prothrombin complex proteins onto a first mass capture means and washing to remove contaminating proteins in a liquid phase;

b) eluting the prothrombin complex proteins from the first mass capture means;

c) converting substantially all of the prothrombin contained in the plasma fraction to thrombin in the presence of a plasmin inhibitor;

d) treating the thrombin so formed with a viricidal agent;

e) sorbing the thrombin onto a second capture means and equilibrating with a physiologic buffer which promotes the binding of thrombin and inhibits the binding of contaminants, and washing with the buffer;

f) eluting the thrombin from the second capture means with a second physiologic buffer; and g) optionally further processing the thrombin by admixing with other physiologic substances to facilitate its intended particular use, concentrating by lyophilization, ultrafiltration, sedimentation, or other means, and storing at a permissive temperature to optimize stability.

In the practice of the present process, it is to be emphasized that all substances contacting the thrombin must be of physiologic suitability, so that the criteria of the U.S. Food and Drug Administration for therapeutic-grade medical biologics are met.

BRIEF DESCRIPTION OF THE DRAWINGS

FIG. 1a and b are rectilinear plots of the profiles of the reverse-phase chromatography of human thrombin.

DETAILED DESCRIPTION OF THE PREFERRED EMBODIMENT

The term "therapeutic", as it relates to thrombin, means that the substance when purified will conform to the standards of purity and identity required by the U.S. Food and Drug Administration for biologics intended for human applications.

A substantially stable therapeutic-grade human thrombin in a therapeutically effective quantity has the following general properties:
1) being substantially viral-safe;
2) having a total nucleic acid content of less than 10 pg per therapeutic dose;
3) being substantially homogeneous;
4) being substantially nonpyrogenic; and
5) having a specific activity of greater than 2200 NIH units/mg protein.

More specifically, therapeutic thrombin is characterized by the following criteria:
1) substantial homogeneity when analyzed by SDS polyacrylamide gel electrophoresis, $C_3$-HPLC chromatography, and immunodifusion;
2) total nucleic acid content of less than 10 pg per therapeutic dose;
3) contamination by blood coagulation Factors VII, IX and X of less than 1 percent by weight in the aggregate;
4) a level of inactivated prothrombin of less than 0.1 percent;
5) a level of inactive prothrombin fragments of less than 5.0 percent;
6) residual viricidal agent content of less than 50 ppm;
7) a specific activity ranging minimally from 2200 NIH units per mg protein to about 3200 NIH units per mg protein;
8) substantial nonpyrogenicity as determined by the limulus amoebocyte lysate (LAL) test; and
9) being substantially free of envelope viruses, by use of a viricidal agent capable of causing minimally 7 logs reduction in viability in spiking experiments.

The thrombin must be obtainable in sufficient large-scale quantities to be practicable and economical in medical applications.

In preparing the thrombin of the present invention the plasma fraction which contains native thrombin and prothrombin is contacted with an ionic species conjugated to a solid matrix under conditions which favor binding thereto of thrombin and its zymogen. The starting material can be any human plasma or fraction thereof which contains the proteins of interest. Typically, a cryopoor fraction from which the coagulation Factor VIII:C has already been removed is utilized for economical and strategic reasons. After adsorption the matrix is extensively washed with a buffer to remove contaminating proteins and other substances which do not bind the matrix under the conditions selected.

In the preferred embodiment, DEAE (diethylamino-ethyl-)-crosslinked agarose is the matrix utilized for the mass capture step because of its excel lent fast flow properties and binding capacities. A form of DEAE-cross-linked agarose having a very large number of binding sites is selected to optimize protein recovery in commercial-scale production.

Other material useful for initial mass capture include virtually any of the commercially available anion exchange celluloses and agaroses including polysulphated agaroses, specifically including but not limited to QAE (quaternary amine) derivatives, DEAE (diethylamino-ethyl) derivatives, Ecteola (epichlorohydrintri-ethanolamine), TEAE (triethylaminoethyl) derivatives, and AE (aminoethyl) cellulose. Fine tuned adjustments in binding and eluting parameters for each of these ion exchange materials will be apparent to those skilled in the art. Excluded from this list are all organic-based resins, the use of which would rule out therapeutic applications.

Sepharose ® derivatives are distinctly preferred over the corresponding Sephadex ® derivatives utilized in the prior art, because of adverse swelling and shrinking properties of Sephadex ®, and its propensity to shed non-filterable particle fragments into the elution buffer. In contrast, Sepharose ® does not shrink and expand with changes in buffer composition, and the 2,3 dibromopropane cross-linked agarose does not exhibit the tendency to shed fragments as does the cross-linked dextrans comprising Sephadex ®.

The mass capture step has two basic functions. One function is to effect partial purification. The other function is to permit, upon elution, concentration of the prothrombin complex into smaller, easy to manage volumes for subsequent process steps. In addition, cold activation of prothrombin may be carried out while it is adsorbed onto the mass capture means.

In the conversion of prothrombin to thrombin, the mass capture eluate comprising a mixture of thrombin, prothrombin, and Factors II, VII, IX, and X, generally referred to as the prothrombin complex, is combined with phospholipids, a source of calcium ions such as calcium chloride and thromboplastin, and incubated for up to several hours at about room temperature. The phospholipids may be a mixture of phosphotidyl serine and phosphotidyl choline, or commercial phospolipid preparations such as Centrolex P ®. The thromboplastin is preferably of human origin, to avoid possible vital contamination from an animal brain source. The most preferred thrombopastin is obtained from recombinant DNA technology.

Conveniently, the viricidal detergents are added immediately following the conversion reaction. Such detergents disrupt the lipid components of envelope viruses, thereby inactivating them. In the preferred embodiment Triton X-100 (1 percent final concentration) and Tween 80 (0.3 percent final concentration) are combined with an organic solvent such as tri-n-butyl phosphate (final concentration 0.3 percent) to inactivate viruses, although other detergents and combinations thereof may be utilized. The so-called chaotropic agents may also be used advantageously in inactivating viruses provided their use does not result in loss of thrombin specific activity.

The conversion reaction also includes a plasmin/plasminogen inhibitor such as transexamic acid, 6-aminohexanoic acid, and related agents. Inclusion of these agents increase yield and specific activity of the thrombin preparation for reasons not altogether clear. The inhibitor naturally reduces plasmin-catalyzed degradations, but also unexpectedly contributes to increased stability of the final product and appears to minimize proteolysis.

Upon completion of the conversion reaction and viral inactivation, the thrombin is contacted with a sulfalkyl-cross-linked agarose as a second mass capture means, which readily binds it at negative pH. This is surprising in that thrombin itself i s negatively charged in the pH range of optimum binding, and therefore could be expected to be repelled by the gel. The sulfalkyl cross-linked agaroses thus appear to possess specific affinity properties for thrombin. In the preferred embodiment of the present invention, sulfopropyl Sepharose ® (S-Sepharose ®) is selected for its uniform bed size under various buffer conditions, its homogeneity of structure, excellent flow properties and adsorptive capacity. Other means exhibiting affinity properties for thrombin include sulfopropyl-Sephadex ®, sulfolated celluloses, dextran sulfate agarose, and heparin agarose.

In contacting the thrombin preparation with the second mass capture means, it is advantageous to dilute first with a physiologically compatible buffer. The buffer selected must promote binding of the thrombin and also aid in the elimination of impurities during washing. The contacting step may be a batch procedure, or conveniently take place in a vertical column or cartridge. In the batch mode, a centrifugation or filtration step is necessary to separate the gel-bound thrombin from the supernatant. The buffers utilized in the elution of thrombin from the second capture means are physiolgically compatible for therapeutic applications and have a pKa of 5.5 to 7.5. Elution with a solution buffered with L-histidine or imidazole is preferred.

Upon elution from the second capture means, the thrombin may be further processed by concentration through lyophilization, ultrafiltration, or other conventional method. Stability of the final product is enhanced by infusion of human albumin, hydroxyethyl starch, dextran, or combinations thereof as a carrier in the range of 1-3 percent w/w. The albumin must, of course, be of therapeutic quality. Finally, the thrombin is packaged in drug vials in one or a plurality of doses, or placed in other such container as may be utilized in specialized applications. Further advantages of the present invention will be apparent from the Examples which follow.

EXAMPLE 1

200 mls of cryopoor human plasma are diluted threefold in 200 mM imidazole, 20 mM sodium citrate, 10 mM sodium chloride buffer pH 7.2. The diluent is applied to a column packed with DEAE- agarose or Sepharose ® and washed exhaustively with the same buffer. Elution is accomplished with 20 mM imidazole, 20 mM citrate, 100 mM sodium chloride at pH 6.5. To the eluate (0.4 volume) is added 0.2 volume freshly prepared Centrolex P (Central Soya) (0.1 percent suspension in 0.15 M NaCl), 0.1 volume thromboplastin (Rabbit Brain Thromboplastin, Baxter International Inc./Dade) 0.04 volume 0.5 M transexamic acid, 0.01 volume IDM calcium chloride, 0.05 volume 1.0 M Tris pH 8.0, 0.05 volume 3.0 M NaCl and 0.15 volume distilled water. After incubation at 25° C. for 30 to 60 minutes a twofold molar excess (with respect to calcium chloride) of solid ethylenediaminetetracetic acid is added. Conversion of prothrombin to thrombin is monitored by a fibrinogen clotting assay. This is followed by addition of 13 ml solvent/detergent mixture (final concentrations 1 percent Triton X-100, 0.3 percent Tween 80 and 0.3 percent tri-n-butyl phosphate respectively). After incubation at 25° C. with stirring for 1 hour, the mixture is applied to a column packed with S-Sepharose ® previously equilibrated with 25 mM L-histidine, 25 mM NaCl pH 6.5. After washing repeatedly, the thrombin is eluted with 25 mM L-histidine, 300 mM NaCl pH 6.5.

The thrombin product so produced had a specific activity of approximately 2400 NIH units/mg protein, is virus-safe, and contains only physiolgically compatible substances.

EXAMPLE 2

The purity of the thrombin prepared according to the method of Example 1 was evaluated utilizing reverse-phase chromatography, an extremely sensitive technique developed for this purpose. The technique was adapted from a method described by Litwiller et al., *Analytical Biochemistry*, 158, 355 (1986), and utilized a $C_3$ column as matrix with an acetonitrile gradient in aqueous trifluoroacetic acid. An Ultrapore RPSC column, 4.6×75 mm (Beckman Instruments), was selected for these studies. A two buffer system utilized a dual-pump HPLC apparatus (Isco Instruments). Buffer A was 0.1 percent (v/v) trifluoroacetic acid (Pierce Chemical Company) in deionized water, and Buffer B was HPLC grade acetonitrile. The gradient is 20 percent A to 50 percent A over 30 minutes at a flow rate of 1.0 ml/minute.

Typical chromatograms of products prepared by the present method are shown in FIG. 1. FIG. 1A reveals a very small leading peak representing minor contamination of the thrombin by beta and gamma thrombin. The major peak corresponds to the position occupied by alpha thrombin. FIG 1B shows a minor contamination by about 3 percent prethrombin-2. None of these preparations contained other vitamin K dependent clotting factors ordinarily found in even highly purified thrombin isolated by conventional methods. The minor impurities are merely alternate forms of thrombin itself, and of no adverse significance therapeutically.

EXAMPLE 3

The pyrogenicity of thrombin prepared according to the method described in Example 1 was evaluated using the bacterial pyrogen test known as the limulus amoebocyte lysate assay, U.S. Pharmacopeia, XXII, 1990, p. 1493. Thrombin was first inactivated with d-phenylalanyl-L-prolinyl-L-arginyl chloromethyl ketone, and diluted to a concentration of 1.0 mg/ml in 20 mM Tris, 20 mM HEPES, 120 mM NaCl, pH 7.0. The value for the endotoxin limit for parenteral drugs (K/M) was calculated for this preparation according to the LAL Validation Guideline of December 1987 issued by the U.S. Food & Drug Administration. For a 1 mg/ml sample of thrombin, the acceptable endotoxin limit is 5000 EU/mg or ml, wherein K is the quantity EU/kg, M is the maximum human dose administered in a 1 hour period (estimated at 1.0ug/kg), and EU is the amount of endotoxin allowed per kg body weight, as obtained from the following equation:

$$K/M = 5.0 \text{ EU/kg}/1.0 \text{ ug/kg} = 5/0.001 = 5000 \text{ EU/mg or ml}$$

The endotoxin content of the thrombin determined experimentally was 663 EU/ml, which is well below the allowable level of 5000 EU/ml.

That which is claimed is:

1. A therapeutic grade thrombin, said thrombin,
  a) being essentially homogeneous when analyzed by SDS polyacrylamide gel electrophoreses, $C_3$-HPLC chromatography, and immunodiffusion;
  b) having a total nucleic acid content of less than 10 pg per therapeutic dose;
  c) being contaminated by blood coagulation Factors VII, IX and X of less than 1 percent by weight in the aggregate;
  d) having a level of inactivated prothrombin of less than 0.1 percent;
  e) having a level of inactive prothrombin fragments of less than 5.0 percent;
  f) having a specific activity ranging minimally from about 2200 NIH units per mg protein to about 3200 NIH units per mg protein; and,
  g) being essentially free of lipid envelope viruses.

* * * * *